United States Patent
Römisch et al.

(10) Patent No.: US 7,202,065 B2
(45) Date of Patent: Apr. 10, 2007

(54) STABILIZED LIQUID PREPARATION OF THE PROTEASE WHICH ACTIVATES BLOOD COAGULATION FACTOR VII, OR OF ITS PROENZYME

(75) Inventors: Jürgen Römisch, Marburg (DE); Annette Feussner, Marburg (DE); Christian Kannemeier, Marburg (DE); Hans-Arnold Stöhr, Wetter (DE)

(73) Assignee: ZLB Behring GmbH, Marburg (DE)

( * ) Notice: Subject to any disclaimer, the term of this patent is extended or adjusted under 35 U.S.C. 154(b) by 973 days.

(21) Appl. No.: 10/033,777

(22) Filed: Jan. 3, 2002

(65) Prior Publication Data
US 2002/0110552 A1    Aug. 15, 2002

(30) Foreign Application Priority Data
Jan. 8, 2001   (DE) ................. 101 00 483
Jun. 25, 2001  (DE) ................. 101 31 404

(51) Int. Cl.
*C12N 9/00*   (2006.01)

(52) U.S. Cl. ................................. 435/183
(58) Field of Classification Search .............. 435/183
See application file for complete search history.

(56) References Cited

U.S. PATENT DOCUMENTS

| 4,082,841 A | * | 4/1978 | Pader |
| 4,296,095 A | * | 10/1981 | Hoppe et al. |
| 4,339,432 A | * | 7/1982 | Ritchey et al. |
| 4,465,662 A | * | 8/1984 | Sato et al. |
| 4,576,816 A | * | 3/1986 | Suganuma et al. |
| 5,589,363 A | * | 12/1996 | Roy et al. |
| 5,604,202 A | * | 2/1997 | Kessler et al. |

FOREIGN PATENT DOCUMENTS

| CA | 2269109 | * | 10/1999 |
| EP | 0 952 215 A2 | | 10/1999 |
| EP | 952215 | * | 10/1999 |
| JP | 2000023696 | * | 1/2000 |

\* cited by examiner

*Primary Examiner*—Michael Meller
(74) *Attorney, Agent, or Firm*—Finnegan, Henderson, Farabow, Garrett and Dunner, L.L.P.

(57) ABSTRACT

A stabilized liquid preparation of a protease which activates blood coagulation Factor VII or of its proenzyme is herein described. The preparation also contains one or more compounds selected from the group consisting of ornithine, diaminopimelic acid, agmatine, creatine, guanidinoacetic acid, acetylornithine, citrulline, arginoinosuccinic acid, tranexamic acid and epsilon-aminocaproic acid or their salts and has a pH of 2–8.

25 Claims, No Drawings

STABILIZED LIQUID PREPARATION OF THE PROTEASE WHICH ACTIVATES BLOOD COAGULATION FACTOR VII, OR OF ITS PROENZYME

The invention relates to a stabilized liquid preparation of the protease which activates blood coagulation factor VII or of its proenzyme which can be stored for several months without showing significant losses of activity or changes in the product.

BACKGROUND OF THE INVENTION

German Offenlegungsschrift 199 03 693 and EP 0952215 A, which are incorporated herein by reference), discloses a protease for activating coagulation factor VII, a process for isolating it, detecting it and inactivating it, and medicinal preparations which comprise this protease or its proenzyme, which is the non-activated form of the protease. It is also reported therein that this protease and its proenzyme suffer, after enrichment or isolation, a rapid loss of activity, which was observed in a solution containing 20 mM Tris, 0.15 mM NaCl at a pH of 7.5. For stabilization, it proposed a preparation which was prepared a) with addition of one or more amino acids in an amount of 0.01 mol/l, preferably more than 0.05 mol/l; and/or b) with addition of a sugar or of a combination of various sugars with a total concentration of more than 0.05 g/ml, preferably more than 0.2 g/ml and/or c) with addition of one or more substances which are able to complex calcium ions, such as citrate, oxalate, ethylenediaminetetraacetic acid etc.

The preparation was moreover adjusted to a pH range from 3.5 to 8.0, preferably to a pH range from 4.0 to 6.8.

Although use of the aforementioned agents achieved considerable success in stabilization, it has proved necessary to look for other stabilizers and stabilizer mixtures which are suitable for use in liquid preparations of said protease and its proenzyme and ensure that such preparations can be stored over prolonged periods, which may amount to several months, without seeing any loss of activity or other changes in the product.

DESCRIPTION OF THE INVENTION

It has now been found that a liquid preparation of the protease which activates blood coagulation factor VII or of its proenzyme is stabilized for prolonged periods, i.e. over several months, if it comprises one or more compounds selected from the group of ornithine, diaminopimelic acid, agmatine, creatine, guanidinoacetic acid, acetylornithine, citrulline, argininosuccinic acid, tranexamic acid and $\epsilon$-aminocaproic acid or one of their salts and derivatives and has a pH between 2.0 and 8.0, preferably 2.5 to 6.8. A pH range of from 3.5 to 6.8 is also suitable.

The stability of a preparation of this type can be improved even further if it additionally comprises a) one or more detergents;

b) one or more sugars;

c) one or more amino acids; and/or d) proteins, preferably albumin, gelatin, fibronectin and vitronectin or similar proteins, and/or e) one or more compounds capable of calcium ion complexation.

The detergents employed are one or more ionic or nonionic surfactants which are known, for example, under the proprietary names Tween® and Triton®. They are generally employed in concentrations between 0.001 and 0.5 percent by weight.

The protease or its proenzyme is used according to the invention in lyophilized form. After the lyophilizate is dissolved, more than 90% of the activity is retained compared with the solution before freeze-drying. The protease and its proenzyme can be kept in solution particularly well if the ionic strength of the solution is greater than 10 mSi. For this purpose, it is necessary to add a sufficient quantity of a salt, for example sodium chloride. The ionic strength is of great importance particularly when protease concentrations over 0.5 mg/ml are used.

Sugars which should be particularly mentioned among those to be used according to the invention for the stabilization are glucose, arabinose or mannose. They can be employed in quantities of 5 to 100 mM.

Amino acids which can be added to the liquid preparation are, in particular, arginine, lysine or glycine. Suitable calcium ion-complexing compounds are, besides citrates, also oxalates and salts of ethylenediaminetetraacetic acid.

The liquid preparations of the protease which activates blood coagulation factor VII or of its proenzyme which are prepared in this way are suitable for pasteurization, nanofiltration or steam/heat viral inactivation. They can be employed as procoagulants either alone or together with substances which increase protease activity, such as heparin or substances related to heparin, such as heparan sulfate, it additionally being possible to add to these agents factor VII in its inactive form. The use of such an agent may be indicated, for example, to exploit its factor VIII-bypassing activity (FEIBA) in cases of intolerance to factor VIII and/or factor IX and/or factor XI and/or the proteins of the contact phase such as factor XII, for example because of the presence of antibodies, or in the presence of other types of deficiency situations. Factor VIII can then be activated either in vivo, in plasma, in enriched fractions or by acting on purified factor VII. The liquid preparation of the invention can also be used ex vivo for general prophylaxis of bleeding or for stopping hemorrhages.

The liquid preparations of the invention can, however, also be employed for thromboembolic disorders or complications like those with leg vein thrombosis, myocardial infarction or strokes.

German Offenlegungsschrift 199 03 693 are EP 0952215 A2 disclose that the protease which activates blood coagulation factor VII can be used for endogenous or exogenous activation of plasminogen activators like prourokinase or sctPA. Because of this property, factor VII-activating protease can be employed for the prophylaxis or therapy of thromboembolic disorders, specifically in combination with single-chain or two-chain plasminogen activators or anticoagulants. The enhancing effect of the factor VII activator on plasminogen activators is particularly promoted by calcium and/or heparin and heparin-like substances such as dextran sulfate. Because of the particular fibrinolytic effect, the preparations of the invention containing the protease which activates blood coagulation factor VII can be employed for the treatment of disorders caused by fibrin-containing thrombi. These include wound healing processes.

It is moreover possible for said protease to be administered intravenously or locally, subcutaneously, intradermally, intramuscularly or else, for injuries or wounds, topically or bound to a suitable carrier matrix. It is possible to employ for this purpose not only the protease or its proenzyme isolated from body fluids such as blood or plasma, but also recombinant or transgenic protease.

The invention claimed is:

1. A stabilized liquid preparation comprising:
   a. a protease or its proenzyme, wherein the protese or its proenzyme activates blood coagulation factor VII;
   b. at least one compound selected from the group consisting of ornithine, diaminopimelic acid, agmatine, creatine, guanidinoacetic acid, acetylornithine, citrulline, argininosuccinic acid, tranexamic acid, and ε-aminocaproic acid or their salts and derivatives; and
   c. wherein said preparation has a pH between 2.0 and 8.0.

2. The stabilized liquid preparation of claim 1, which additionally comprises at least one ionic detergent.

3. The stabilized liquid preparation of claim 1, which additionally comprises at least one nonionic detergent.

4. The stabilized liquid preparation of claim 2, wherein the ionic detergent is present in an amount ranging from 0.001 to 0.5 percent by weight of the liquid preparation.

5. The stabilized liquid preparation of claim 3, wherein the nonionic detergent is present in an amount ranging from 0.001 to 0.5 percent by weight of the liquid preparation.

6. The stabilized liquid preparation of claim 1, wherein the pH is between 2.5 and 6.8.

7. The stabilized liquid preparation of claim 1, wherein the pH is between 3.5 and 6.8.

8. The stabilized liquid preparation of claim 1, wherein the liquid preparation additionally comprises:
   a. at least one detergent;
   b. at least one sugar;
   c. at least one amino acid; and optionally.

9. The stabilized liquid preparation of claim 8, wherein the detergent is at least one ionic detergent.

10. The stabilized liquid preparation of claim 8, wherein the detergent is at least one nonionic detergent.

11. The stabilized liquid preparation of claim 8, wherein the detergent is present in an amount from 0.001 to 0.5 percent by weight of the liquid preparation.

12. The stabilized liquid preparation of claim 8, wherein the at least one sugar is selected from the group consisting of glucose, arabinose, and mannose.

13. The stabilized liquid preparation of claim 8, wherein the at least one amino acid is selected from the group consisting of arginine, lysine, and glycine.

14. The stabilized liquid preparation of claim 1, wherein the ionic strength of the liquid preparation is adjusted to greater than 10 mSi by addition of a salt.

15. The stabilized liquid preparation of claim 8, wherein the ionic strength of the liquid preparation is adjusted to greater than 10 mSi by addition of a salt.

16. The stabilized liquid preparation of claim 1, wherein the protease or its proenzyme is in lyophilized form.

17. The stabilized liquid preparation of claim 8, wherein the protease or its proenzyme is in lyophilized form.

18. The stabilized liquid preparation of claim 1, wherein the protease or its proenzyme is present in an amount greater than 0.5 mg/ml.

19. The stabilized liquid preparation of claim 8, wherein the protease or its proenzyme is present in an amount greater than 0.5 mg/ml.

20. A pharmaceutical composition comprising the stabilized liquid preparation of claim 1.

21. A diagnostic reagent comprising the stabilized liquid preparation of claim 10.

22. A method of treating thromboembolic disorders by administering to a mammal, the pharmaceutical composition according to claim 20.

23. A method of treating complications associated with leg vein thrombosis, myocardial infarction, or stroke by administering to a mammal, the pharmaceutical composition according to claim 20.

24. A method of treating disorders caused by fibrin-containing thrombi by administering to a mammal the pharmaceutical composition according to claim 20.

25. The stabilized liquid preparation of claim 8, wherein the liquid preparation additionally comprises at least one complex with a calcium ion.

* * * * *